United States Patent [19]
Horwitz et al.

[11] Patent Number: 5,837,677
[45] Date of Patent: Nov. 17, 1998

[54] METHOD FOR THE TREATMENT OF CANCER WITH EXOCHELINS OF *MYCOBACTERIUM TUBERCULOSIS*

[75] Inventors: Lawrence D. Horwitz; Kathryn B. Horwitz, both of Englewood, Colo.

[73] Assignee: Keystone Biomedical, Inc., Los Angeles, Calif.

[21] Appl. No.: 882,122

[22] Filed: Jun. 25, 1997

Related U.S. Application Data

[63] Continuation-in-part of Ser. No. 383,180, Feb. 3, 1995, Pat. No. 5,721,209.
[51] Int. Cl.$^6$ ..................................................... A61K 38/12
[52] U.S. Cl. .................. 514/11; 514/17; 514/18; 530/317; 530/329; 530/330; 435/71.2; 435/118; 435/120; 435/863; 435/864; 435/865; 435/866; 540/524; 540/526
[58] Field of Search .................... 514/11, 17, 18; 530/317, 329, 330; 435/71.2, 118, 120, 863, 864, 865, 866; 540/524, 526

[56] References Cited

PUBLICATIONS

Blatt, Julie et al., "Failure to Alter the Course of Acute Myelogenous Leukemia in the Rat with Subcutaneous Deferoxamine," *Leukemia Research* vol. 15, No. 5, pp. 391–394, 1991.
Brodie, Chaya et al., "Neuroblastoma Sensitivity to Growth Inhibition by Deferrioxamine: Evidence for Block in $G_1$ Phase of the Cell Cycle," *Cancer Research* 53, 3968–3975, Sep. 1, 1993.
Crowley, Stephen T. et al., "Platelet–Induced Vascular Smooth Muscle Cell Proliferation is Moderated . . . ," *Circulation* vol. 90, No. 4, 1908–1918, Oct. 1994.
Donfrancesco, Alberto et al., "Effects of a Single Course of Deferoxamine in Neuroblastoma Patients," *Cancer Research* 50, 4929–4930, Aug. 15, 1990.
Gobin, Jovana et al., "Exochelins of *Mycobacterium Tuberculosis* Remove Iron from Human Iron–Binding Proteins and Donate Iron to Mycobactins in the *M. Tuberculosis* Cell Wall," *The Journal of Experimental Medicine* vol. 183, No. 4, Apr. 1, 1996.
Gobin, Jovana et al., "Iron Acquisition by *Mycobacterium Tuberculosis*: Isolation and Characterization of a Family of Iron–Binding Exochelins," *Proc. Natl. Aca. Sci. USA* vol. 92, pp. 5189–5193, May 1995.
Lloyd, John B. et al., "Evidence that Desferrioxamine Cannot Enter Cells by Passive Diffusion," *Biochemical Pharmacology*, vol. 41, No. 9, pp. 136–1363, 1991.
Graham, Mark L. et al., "Simultaneous Measurement of Progesterone Receptors and DNA Indices by Flow Cytometry: Characterization of an Assay in Breast Cancer Cell Lines," *Cancer Research*, 49, 3934–3942, Jul. 15, 1989.
Reddel, Roger R. et al., Cell Cycle Effects of Iron Depletion on T–47D Human Breast Cancer Cells, *Experimental Cell Research* 161, 277–284, 1985.
Renton, Fiona J. and Thomas Jeitner, "Cell Cycle–Dependent Inhibition of the Proliferation of Human Neural Tumor Cell Lines by Iron Chelators," *Biochemical Pharmacology*, vol. 51, pp. 1553–1561, 1996.
Richardson, Des. and Prem Ponka, The Iron Metabolism of the Human Neuroblastoma Cell: Lack of Relationship Between the Efficacy of Iron Chelation and the Inhibition of DNA Synthesis, *J Lab Clin Med*, vol. 124, No. 5, 660–671, 1994.
Summers, M.R. et al., Studies in Desferrioxamine and Ferrioxamine Metabolism in Normal and Iron–Loaded Subjects, *British Journal of Haematology*, 42, 547–555, 1979.

*Primary Examiner*—Frederick Krass
*Attorney, Agent, or Firm*—Loeb & Loeb LLP; Michael J. Ram

[57] ABSTRACT

The invention is directed toward the use of desferri-Exochelins to destroy cancer cells or retard or eliminate the growth of those cancer cells.

5 Claims, 6 Drawing Sheets

FIG. 1A
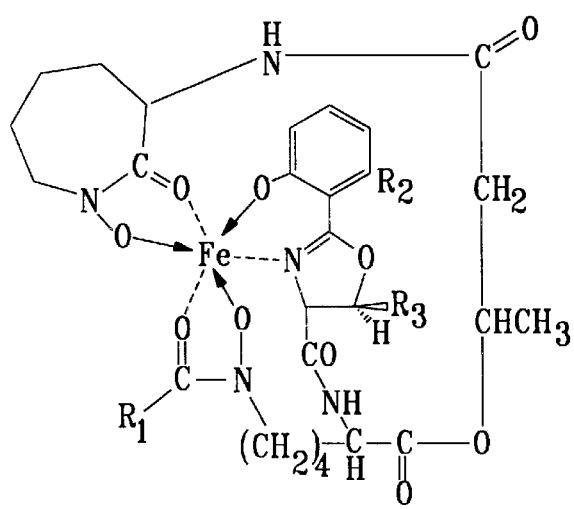
FERRIEXOCHELIN
FIG. 1B
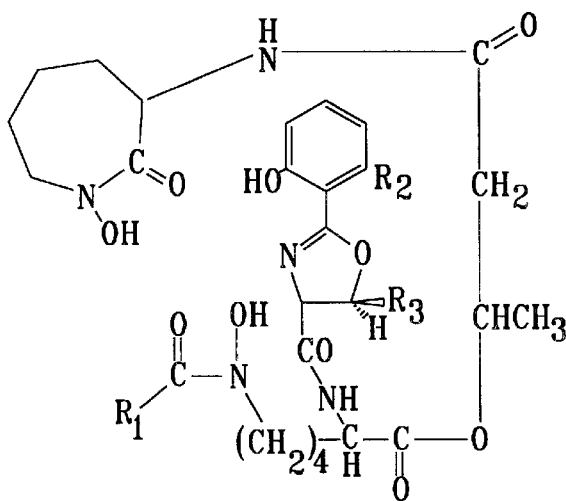
DESFERRIEXOCHELIN
| $R_1$ | | $R_3$ | $M_r$ |
|---|---|---|---|
| $(CH_2)_N COOCH_3$ | N=1–7 | $H, CH_3$ | 716–828 |
| $(CH_2)_x CH=CH(CH_2)_y COOCH_3$ | x+y=1–5 | $H, CH_3$ | 742–826 |
FIG. 1C

METHOD FOR THE TREATMENT OF CANCER WITH EXOCHELINS OF *MYCOBACTERIUM TUBERCULOSIS*

The present invention is a continuation-in-part of U.S. Ser. No. 08/383,180, filed Feb. 3, 1995, now U.S. Pat. No. 5,721,209. It is directed to the treatment of cancer using Exochelins of Mycobacterium tuberculosis to prevent proliferation of and to kill cancer cells.

BACKGROUND OF THE INVENTION

Rapid growth of abnormal cells is characteristic of cancer, and the prevention of proliferation of cancerous cells or their destruction are major goals of cancer chemotherapy. Since iron is necessary for cell proliferation, drugs that deprive cancer cells of iron are among the potential therapies for cancer. Deferoxamine, an iron chelator, has been reported to inhibit proliferation of cultured human neuroblastoma cells (Brodie et al, *Cancer Res* 53:3968–3975, 1993). In this publication, neuroblastoma cells treated with deferoxamine were consistently blocked at an early point in the cell cycle (the G1 phase) before initiation of DNA synthesis. In another study deferoxamine inhibited proliferation of cultured human breast cancer cells (Reddel, R. et al, *Experimental Cell Res* 161:277–284, 1985). However, others have reported that deferoxamine has limited value in treatment of patients with neuroblastoma (Donfresco, A et al, *Cancer Res* 50:4929–4930, 1990). In another report (Renton, F. J. et al, *Biochemical Pharm* 51;1553–1561, 1996) iron chelation with deferoxamine had differing effects on the stage of cell cycle inhibition and the degree of growth suppression of neural tumor cell lines, depending on drug concentration and the time of treatment. Deferoxamine was ineffective in altering the course of acute myelogenous leukemia in a rat model (Blatt, J et al, Leuk Res 15:391–394, 1991).

Despite its effectiveness in some models, deferoxamine, a compound that is not extractable in chloroform and is therefore not soluble in lipids, has limitations as a treatment for cancer. Deferoxamine can only be given intravenously, can enter cells or tissues only very slowly by pinocytosis, and requires continuous administration because it is rapidly excreted (Lloyd et al, *Biochem Pharmacol*; 41:1361–1363, 1991). There are significant side effects when deferoxamine is administered in high doses in vivo, and levels higher than 10 $\mu$mol/L cannot be achieved under usual conditions (*Br J Haematol* 1979;42:547–555). Based on in vitro studies cited above, these levels are not high enough to have an effective anti-proliferative effect in patients. Even if adequate levels could be attained, the expense and inconvenience of repeated prolonged intravenous infusions of this drug, which cannot be administered by other routes, would be a major disadvantage for treatment of cancer. Therefore, although deferoxamine has been effective in some cell culture models of cancer, the drug has pharmacokinetic properties that make it unattractive for use to treat patients with cancer.

Certain other iron chelators, namely pyridoxal isonicotinoyl hydrazone (PIH) and some of its chemical analogs, were more effective than deferoxamine in preventing iron uptake by, and increasing iron release from, human neuroblastoma cells in culture (Richardson D. R. and Ponka P, *J Lab Clin Med*, 124:660–671, 1994). However, PIH was no more effective than deferoxamine at preventing tritiated-thymidine incorporation, a measure of the DNA synthesis that precedes cell division. Although PIH does not appear to be promising, these results do not exclude the possibility that other novel iron chelators, particularly ones with either higher affinity for iron or with biochemical and pharmacokinetic properties that enhance capacity to rapidly enter cells or allow oral or transcutaneous administration, might be more useful than deferoxamine, for treatment of cancer.

Exochelins of Mycobacterium tuberculosis are iron chelators with certain special biochemical characteristics that make them attractive for treatment of cancer by chelation. Desferri-Exochelins have a very high affinity for iron and are capable of removing iron from the iron binding proteins transferrin and ferritin, which are the principal sources of iron in cells (Gobin J and Horwitz M, *J Exp Med* 183:1527–1532, 1996). In addition they differ from deferoxamine in being highly soluble in lipids (Gobin J et al, *Proc Natl Acad Sci USA* 92:5189–5193, 1995), which enhances their ability to enter cells and alters their subcellular localization. The lipid solubility of desferri-Exochelins may allow oral or other routes of administration, and there is potential for small doses to more rapidly and effectively enter cells compared with deferoxamine, which is not lipid soluble. These and other characteristics of Exochelins of *M. tuberculosis* render them more efficacious than deferoxamine for treatment of cancer.

Therefore, there is a need for a more universally applicable, nontoxic, easily administered treatment for cancer. This need could be met by providing an agent that, like deferoxamine, is capable of iron chelation and preventing cell growth, but, in contrast to deferoxamine, is lipid-soluble. A lipid-soluble iron chelator with these properties is potentially capable of oral or transcutaneous administration, to enter cancer cells rapidly in low non-toxic doses, to prevent cancer cell growth and to kill cancer cells.

SUMMARY

These needs are met by the present invention which comprises the use of Exochelins to prevent the proliferation of human cancer cells and more particularly breast cancer cells. In particular, the invention is directed to the administration of Exochelins by any of several routes potentially suitable to a lipid-soluble agent that is also soluble in water, such as the oral, transcutaneous, and parenteral routes, to patients with cancer to prevent cancer cell growth and kill cancer cells.

Also presented is the chemical structure of Exochelins and modified Exochelins as well as other applications of these materials in the treatment and diagnosis of disease in mammals.

DRAWINGS

These and other features, aspects and advantages of the present invention will become better understood with reference to the following description, appended claims, and accompanying drawings, where:

FIGS. 1A and B show the general chemical structure of an iron chelate of Exochelin (ferri-Exochelin) and the desferri-Exochelin (iron free) molecule, respectively, with the variations of the chemical structure of R1 and R3 side chains and the masses of the various molecules being set forth in FIG. 1C.

FIGS. 2A and B show elution profiles of a culture filtrate of *M. tuberculosis* monitored at 220 nm and 450 nm, respectively.

Figure 7A:
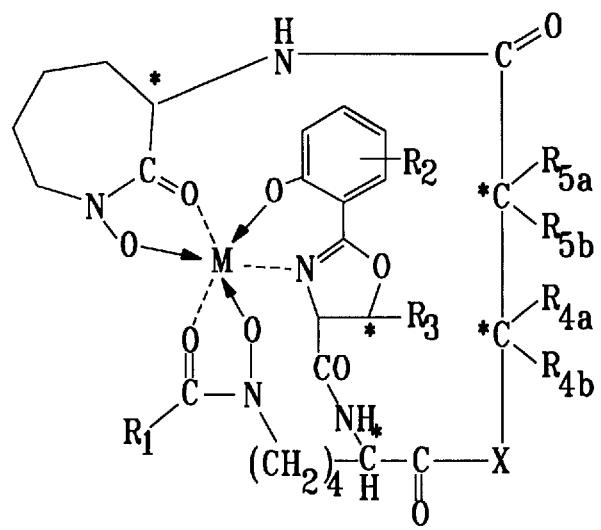

FIGS. 7A and B show the chemical structure of an iron chelate of Exochelin (ferri-Exochelin) and the desferri-Exochelin (iron free) molecule with locations for modification identified.

DETAILED DESCRIPTION OF THE INVENTION

Both desferri-Exochelins and ferri-Exochelins of *Mycobacterium tuberculosis* have been demonstrated to be capable of preventing proliferation of human breast cancer cells.

Applicants, in their parent application, have shown that Exochelins can block, or significantly reduce, oxidative damage to tissue resulting from the iron-mediated catalysis of tissue/free radicals reactions, such as the hydroxyl radical (●OH), particularly hydroxyl radicals generated in the Fenton reaction, commonly referred to as reperfusion injury. It has been further found that the Exochelins are effective to retard or prevent reperfusion injury when administered at the start of or concurrent with reperfusion. Additionally, it has been found that Exochelins encompass a much broader class of materials and have a different chemical structure then originally theorized by Macham et al., *J. General Microbiology* 89:279–282, (1975) and Barclay et al, *J. General Microbiology* 134:771–776, (1988).

It has also been found that these materials can chelate a broad range of metals to result in materials not previously known. Besides preventing reperfusion injury, properly modified Exochelins can be used to treat certain diseases, attack certain cells, such as cancer cells, and be used to monitor the effectiveness of drug treatment and detect the presence of certain disease states. In particular, it is known that the growth of neuroblastoma cells can be negatively affected by the removal of iron using the iron chelating compound desferrioxamine without similarly affecting the growth of normal cells. Other applications of Exochelins include treatment of iron overload from transfusions or cancer chemotherapy, particularly for leukemia.

As a result of isolating and purifying Exochelins, it has been found that Exochelins are a family of molecules having a range of molecular weights and various different side chains. Further, purified Exochelins have been prepared and their utility as scavengers of free iron, such that they are effective in preventing the formation of tissue damaging hydroxyl radicals (●OH), has been demonstrated for the first time. In particular, purified Exochelins of *M. tuberculosis* have been isolated and have been shown to effectively remove iron from transferrin, lactoferrin and ferritin at physiological pH without transmitting any of the infectious properties of the bacteria from which they are derived. It has also been demonstrated for the first time that these Exochelins block hydroxyl radical formation by the Fenton reaction and, based on the response of cardiac myocytes, can be effective to prevent reperfusion injury after myocardial infarction or vascular insults to other tissue when administered after the attack occurs as well as for several hours after the episode.

While mycobactins have been extensively studied, individual Exochelins had not been isolated or purified and their structure and composition had not been previously defined. Further, we have found that prior references have mischaracterized the Exochelins, and thus have failed to identify the structure of these compounds. In particular, Macham (ibid.) identified them as a penta- or hexapeptide, having a molecular weight of 750 to 800, containing 3 mol of ε-N-hydroxylysine, εN-acetyl-εN-hydroxylysine, or εN-hydroxyornithine and 1 mol of threonine. We have found that the Exochelins have a much broader range of molecular weights, constitute several series of compounds with an identifiable difference in molecular weights, include only 2 mol of ε-N-hydroxylysine and are not peptides. A peptide is a polymer of an amino acid ($NH_2$—CHR—COOH) formed by the condensation of the carboxylic group of a first molecule with the amino group of another molecule to form an amide linkage (—CO—NH—). Exochelins cannot be considered to be peptides. Instead, they contain three amino acids and other structural moieties (salicylic acid, dicarboxylic acids or monoester analogs, and hydroxy carboxylic acids) formed by amide (—NH—CO—), hydroxymate (—NH(OH)—CO—) and ester condensations (—CO—O—). The ferri- and desferri forms are shown in FIG. 1.

Preparation

Exochelins were generated and purified from a virulent (Erdman) and avirulent (H37Ra) strain of *M. tuberculosis*. To enhance the production of *M. tuberculosis* Exochelins, the bacteria were cultured in an iron deficient medium. In particular, the Erdman strain of *M. tuberculosis* (American type culture collection 35801) and H37Ra (ATCC 25177) were grown on Middlebrook 7H11 agar plates at 37° C. in 5% $CO_2$. After 14 days the bacteria were harvested, suspended in 150 ml of modified Sauton's medium in culture flasks and incubated for 3 to 8 weeks. The modified Sauton's medium contained 0.12 mg/l ferric ammonium citrate without added surfactant.

Iron rich Exochelins (ferri-Exochelins) were then recovered by filtering, saturating with iron, extracting with chloroform, and purification by high pressure liquid chromatography (HPLC). Specifically, the supernatant fluid from the above suspension was filtered through successive 0.8 μm and 0.2 μm low-protein binding filters. The Exochelins were then loaded with iron by saturating the filtered supernatant fluid by exposure to ferric chloride (150 mg per liter of culture filtrate). The ferric-Exochelins were mixed with chloroform (1 volume of culture filtrate per 1.5 volumes of chloroform) and, after separation of the layers, the Exochelin rich chloroform layer was removed and stored under anhydrous magnesium sulfate (2 g/l). The chloroform extract was then passed through a fritted glass filter and evaporated by rotary evaporation leaving behind a brown residue.

The brown residue was further purified by suspension in 5 ml of a first buffered solution (0.1% trifluoroacetic acid) which was introduced into a liquid chromatography column (C-18 Sep-Pak cartridge). The brown band which formed near the top of the column was eluted with a second buffer (0.1% TFA, 50% acetonitrile). The partially purified material was then diluted three-fold in 0.1% trifluoroacetic acid and subjected to reverse phase high pressure liquid chromatography at a rate of 1 ml/min followed by exposure to a C-18 column. The presence of the iron rich Exochelins in the HPLC eluate was detected by simultaneous monitoring of the UV absorbance of the 450 nm peak (iron compounds) and the 220 nm peak which is indicative of amide and aromatic groups. Approximately 5 major and 10 minor peaks, shown in FIG. 2, eluted out of the final C-18 column exhibited a high 450/220 nm absorbance ratio. These were confirmed to be Exochelins by mass spectrometry. Major peaks were further purified by a second reverse phase HPLC on an alkyl-phenyl column. The Exochelins recovered from the Erdman strain of *M. tuberculosis* were identical to the Exochelins recovered from the H37Ra strain.

Characterization

Figure 2A:
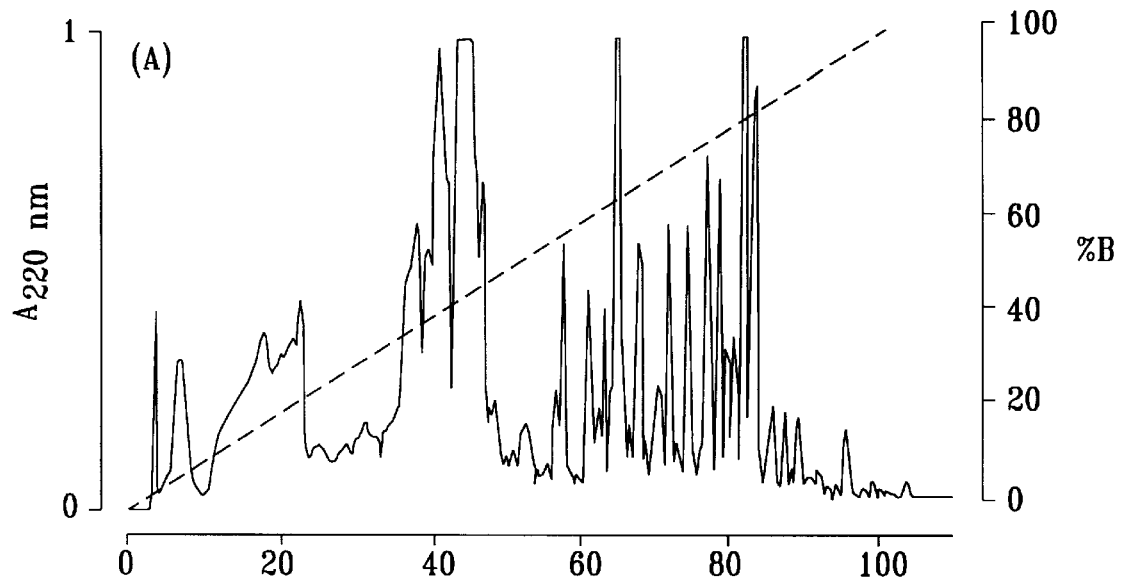
Figure 2B:
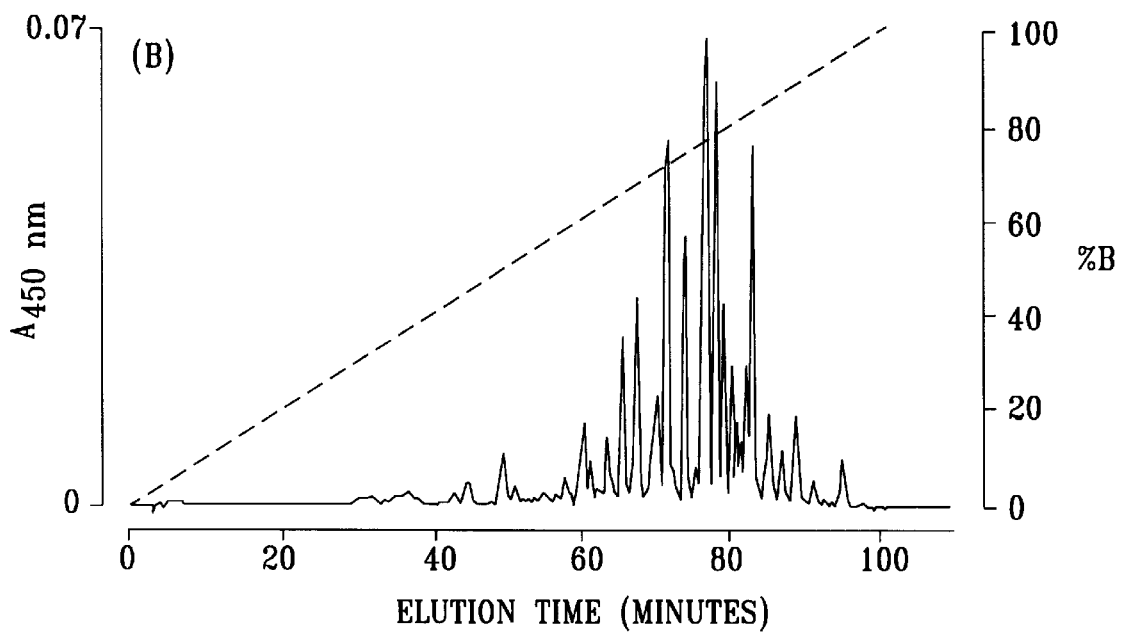
Figure 3:
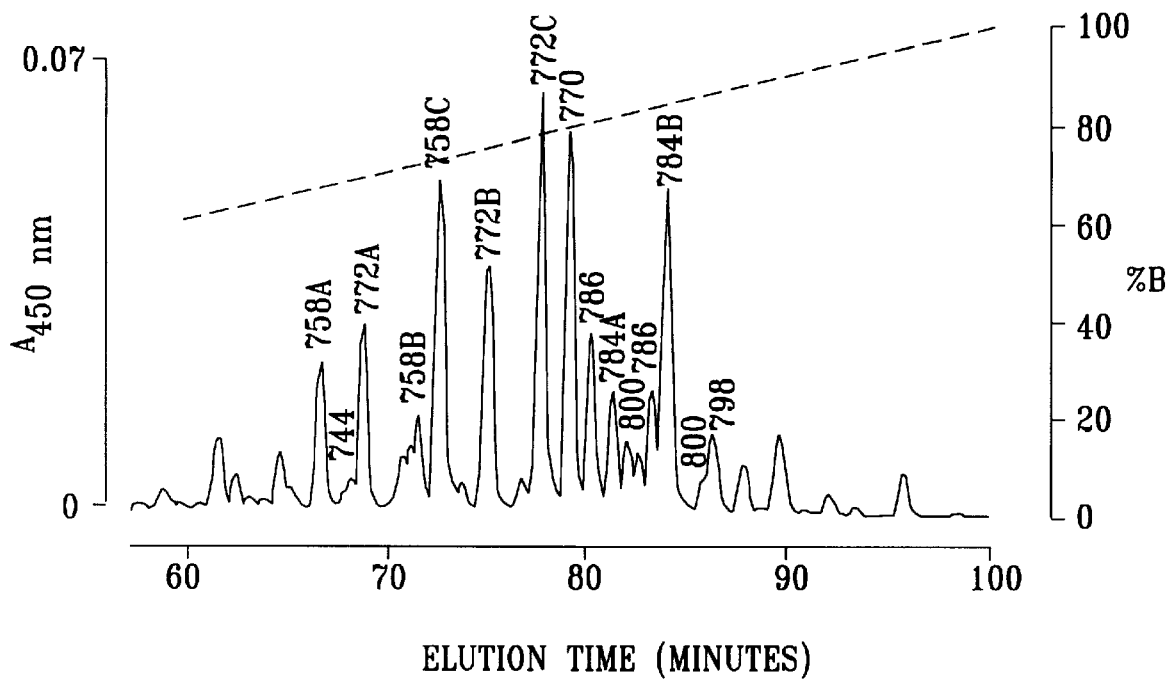
FIG. 3 shows an elution profile of the same filtrate monitored at 450 nm with the molecular weight of each peak shown.
Figure 4B:
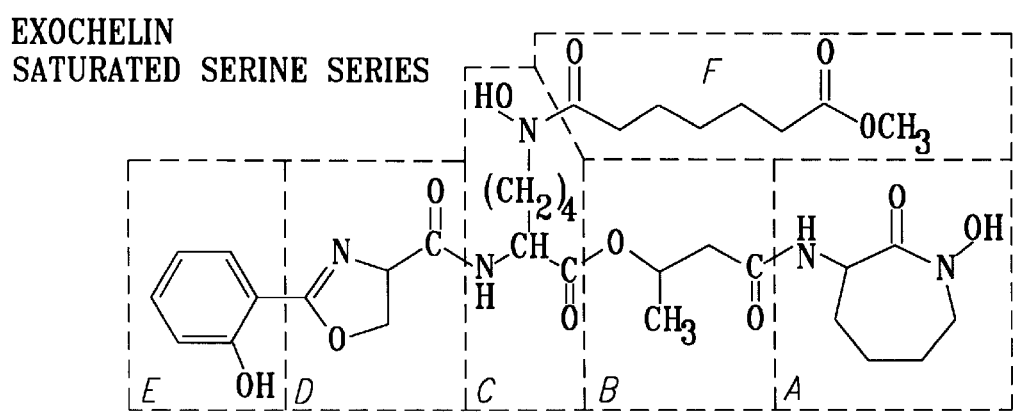
FIG. 4A shows the mass spectrometer spectra of a major serine-containing Exochelin at m/z=720.3, the structure determined therefrom being shown in FIG. 4B.
Figure 4A:
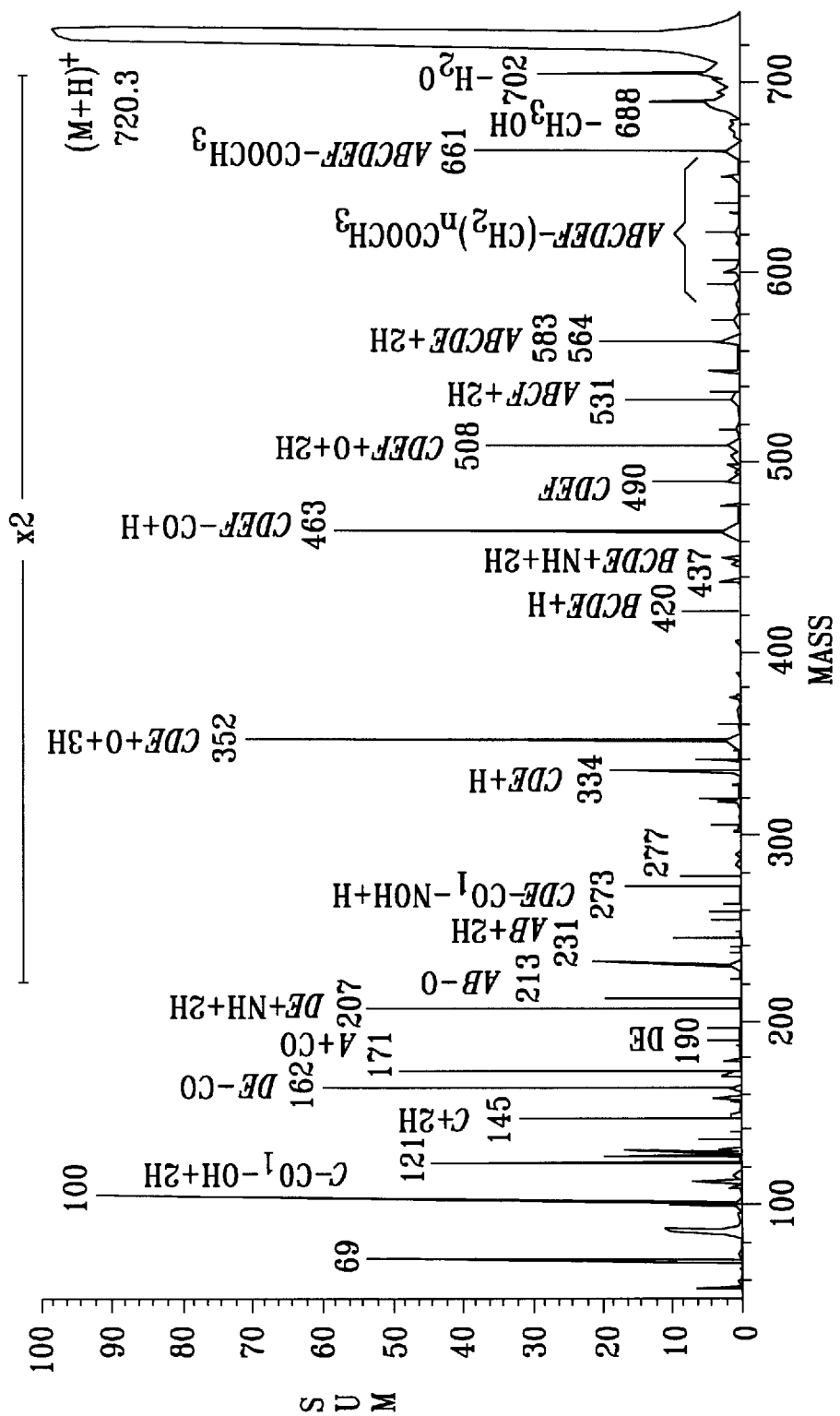

Based on liquid secondary ion mass spectrometry (LSIMS) and electrospray ionization mass spectrometry (ESI-MS) analysis of the numerous in their ferri-($Fe^{3+}$) form, eluted from the column (see FIG. 3), the iron-peaks Exochelins are not confined to the iron-loaded form of the molecules detailed in FIG. 4, but include a family of species ranging in mass from 716 to 828 daltons. Each member of the family appears to differ from its neighbor by 14 daltons, reflecting the number of $CH_2$ groups in the $R_1$ alkyl side chain and/or 2 daltons, reflecting the presence of a double bond in the $R_1$ alkyl side chain. Accordingly, the Exochelins appear to form two series with the subsequent members of each series differing in mass by 14 daltons, the saturated series having masses of approximately 716, 730, 744, 758, 772, 786, 800, 814 and 828 daltons and the unsaturated series having masses of 742, 756, 770, 784 798, 812 and 826. Additionally, the presence or absence of a methyl group at $R_3$ (i.e., H or $CH_3$) further defines an additional two series of molecules referred to as the serine ($R_3$=H) and the threonine series ($R_3$=$CH_3$), as confirmed by amino acid analysis. The most polar compounds are to the left of the figure (elute earlier) and the least polar (most soluble in lipid) are to the right. However all the peaks are water soluble. Where more than one peak was found to have the same molecular weight each peak is further designated A, B or C (i.e., 758A, B and C) to indicate the level of polarity with A representing the more polar compound and the C representing the less polar form. The more polar forms are believed to result from a methyl groups attached at different location in the molecule.

Structure of the Exochelin

FIG. 4 shows the results of tandem mass spectrometric analysis under induced dissociation (He floated at 2 keV for a collision energy of 6 keV) of the major saturated serine-containing desferri-Exochelin with $(M+H)^+$ at m/z 720.3. The fragment ions were assigned to one of the six structural moieties A-F resulting from the cleavage products generated about the amide or ester bonds with the hydrogen transfer relative to the neutral molecule associated with each peak indicated on the spectrum shown in FIG. 4. Acid hydrolysis and methylation of the Exochelins resulted in the formation of salicylic acid and pimelic acid. The mass spectrographic analysis indicates that the pimelic acid is present in the Exochelin as a methyl ester.

Figure 7B:
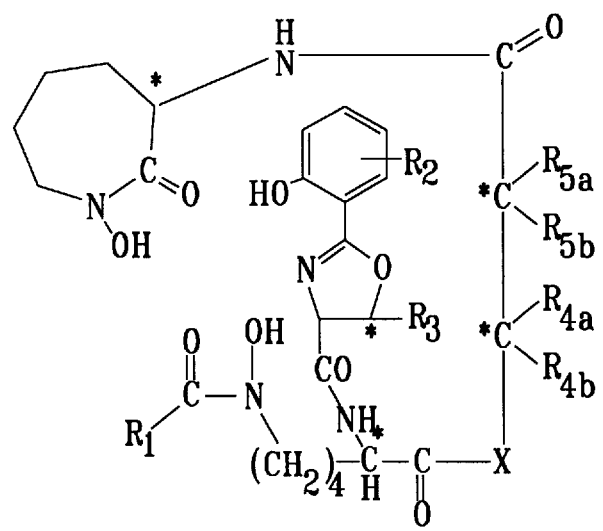

Based on this analysis the general structure of the ferri-Exochelins and the desferri-Exochelins is shown in FIG. 1. The methyl group shown at the $R_4$ position (as defined in FIGS. 7A and 7B) may be in the $R_5$ position. The iron-Exochellin core molecule is circular with iron in the center. It contains 3 amino acid moieties (two N-hydroxylysines and 1 serine or threonine, depending on whether $R_3$ is a hydrogen or methyl group). The major difference between Exochelins and mycobactins of *M. tuberculosis* is that $R_1$ in the Exochelins exists as either a saturated alkyl methyl ester (($CH_2$)$_N$$COOCH_3$) or a singly unsaturated alkyl methyl ester ($CH_2$)$_x$$CH$=$CH$($CH_2$)$_y$$COOCH_3$ and Exochelins have a much shorter alkyl side chain than mycobactins with these shorter side chains terminating in methyl ester moieties. These differences provide for the water solubility of the Exochelins and their ability to function in the extracellular environment.

Clinical Utility

The clinical utility of the administration of Exochelins to prevent cancer cell proliferation was demonstrated by treatment of cells from the T47D-YB human breast cancer cell line grown in vitro.

Cells from the T47D-YB human breast cancer cell line were grown in flasks, initially in 5% fetal calf serum and then in 2% fetal calf serum. The cells were then plated for two days in 6-well dishes at a density of 200,000 cells per well with each well containing 2 ml of medium containing 2% fetal calf serum. On the third day (Day 0) treatment was begun. The wells were divided into a) untreated (control) wells to which 50 μl phosphate buffered saline (PBS) was added; b) wells treated with 50 μM deferoxamine; c) wells treated with 20 μM desferri-Exochelin 770SM, and d) wells treated with 20 μM ferri-Exochelin 770 SM, also referred to as 770 C in accordance with the discussion above under Characterization. The treatment period was four days. The desferri- and ferri-Exochelin (770 SM), indicated in FIG. 6, have a mass of 717 and 770 respectively.

Prior to initiation of treatment (on Day 0), samples for cell counts were removed from duplicate untreated wells. After treatments were initiated, samples were obtained in duplicate from all four groups after one, two, three, and four days of treatment. Cells were washed, resuspended and manually counted in a hemacytometer (Crowley et al, Circulation 90:1908–1918, 1994). Parallel duplicate sets of cells were separately harvested for flow cytometry from untreated wells just prior to initiation of treatments, and from all groups after one day of treatment. Analysis of cell progression through the mitotic cell cycle was performed by flow cytometry after trypsinization, centrifugation, clearing of ribonucleic acid (RNA) with RNAase, and staining of deoxyribonucleic acid (DNA) with propidium iodide. Cells were analyzed with a fluorescence-activated cell sorter, and the percentage of cells in the G0/G1, S and G2-M phases of the cell cycle was determined (Graham M. L. II et al, Cancer Res 49:3934–3942, 1989). Cells in the G0/G1 phase are non-proliferative, whereas cells in the S and G2 phases undergo DNA synthesis and replication, both of which immediately precede cell division, or mitosis (M phase).

Figure 6:
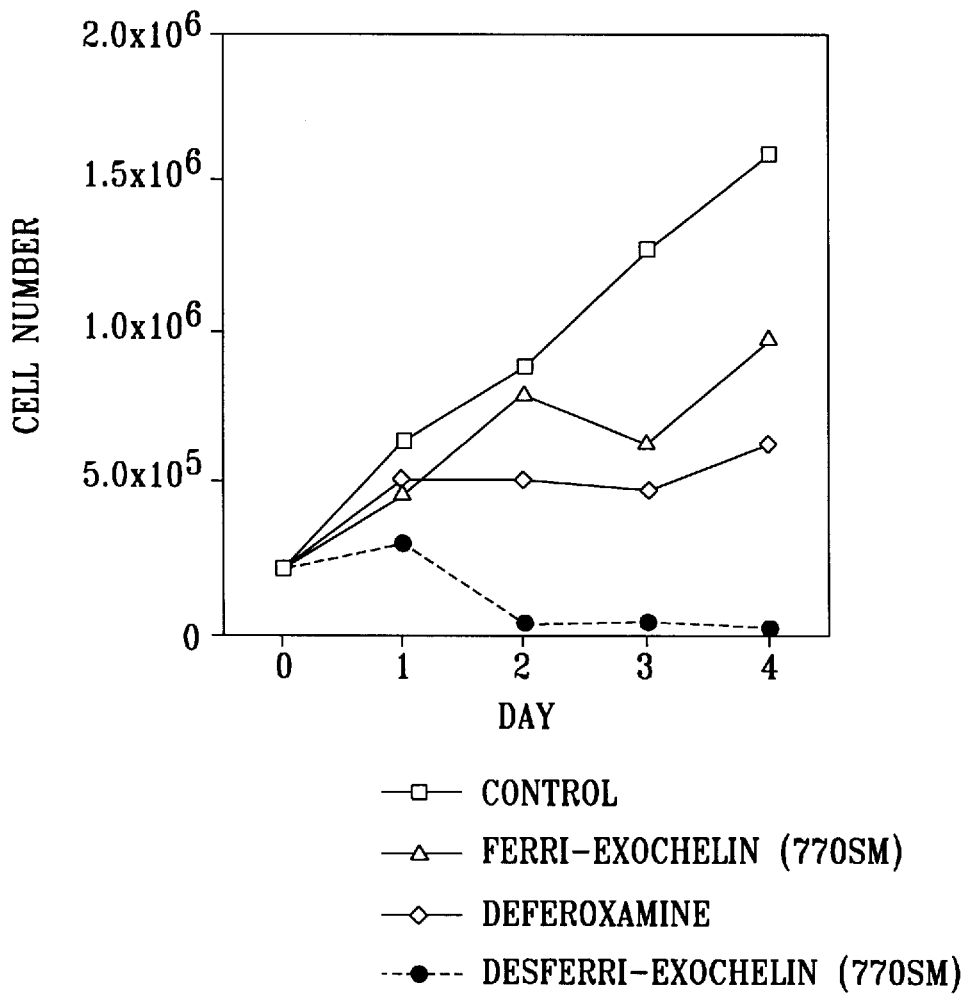
FIG. 6 is a graph of comparative results showing the number of breast cancer cells present during four days of treatment.

Results of the cell counts are shown in FIG. 6. In the control wells (PBS) there were increases in the number of cells/well by similar increments each day. Cell counts increased from an initial mean cell count of 220,000/well prior to initiation of all treatment regimens to a mean cell count of 1,590,000/well on Day 4. Cell proliferation was inhibited to different degrees in each of the three treated groups. In the wells treated with ferri-Exochelin, there was modest inhibition of cell counts relative to the control the first two days and more marked inhibition the third and fourth days. The cell count on Day 4 in the ferri-Exochelin wells was 970,000/well. Although this shows evidence of substantial cell proliferation, this cell count was 45% less than in the control wells. In the wells treated with deferoxamine, there was more marked inhibition of cell counts relative to the control wells, although some cell proliferation occurred. The mean cell count on Day 4 in the deferoxamine-treated wells was 620,000/well; a 70% decrease compared with the control wells. In contrast to the deferoxamine and ferri-Exochelin, in the wells treated with desferri-Exochelin, there was not only complete inhibition of cell proliferation, but cell counts decreased below the original number plated, beginning on the second day. Cell counts in the desferri-Exochelin-treated wells were 295,000/well on treatment Day 1, fell to 32,750 on Day 2, 41,400 on Day 3 and 20,000 on Day 4. Thus, the desferri-Exochelin not only prevented cell proliferation but also resulted in extensive destruction of the breast cancer cells.

In summary, there was an approximately seven fold growth of these cancer cells in the control wells, a four fold growth in the cells treated with ferri-Exochelin, a three-fold growth in the cells treated with deferoxamine, and no growth with destruction of greater than 90% of the cells treated with the desferri-Exochelin.

TABLE 1

Flow Cytometry Analysis Of Cell Cycle Progression in Cancer Cells.

| | Day | % cells in G0/G1 phase (non-proliferative) | % cells in S / G2-M phase (growth fraction) |
|---|---|---|---|
| Pretreatment | 0 | 59.7 | 40.3 |
| Control | 1 | 53.3 | 46.7 |
| Deferoxamine | 1 | 44.9 | 55.1 |
| Ferri-Exochelin | 1 | 60.5 | 39.5 |
| Desferri-Exochelin | 1 | 81.3 | 18.7 |

The results of the mitotic cell cycle analyses by flow cytometry, performed on duplicate wells prior to treatment and on Day 1 of treatment are shown in Table 1. The percentage of cells in the S plus G2-M phases of the cell cycle are representative of the "growth fraction". The remaining cells are in the nonproliferative G0/G1 phases. In the cells obtained prior to treatments (Day 0) 40.3% were in either S or G2-M, the phases involving DNA synthesis and mitosis that result in cell growth. After one day of treatment (Day 1), a slightly higher percentage of the control cells (PBS treated) shifted from G0/G1 into the S/G2-M phases with 46.7% of the cells in S/G2-M. In the wells treated with ferri-Exochelin, there was no change from the result in the pretreatment wells with 39.5% of the cells in the S/G2-M phase, indicating some inhibition of the shift into the growth fraction which occurred in the control cells. In contrast in the wells treated with deferoxamine there was an increased shift out of G0/G1 into the growth fraction compared with the control wells, with 55.1% of the cells in the S/G2-M phases. In the wells treated with desferri-Exochelin there was a dramatic decrease in the percentage of cells in the growth fraction as compared with either the pretreatment cells or the control cells. Only 18.7% of the cells were in the S/G2-M phase, whereas the remaining cells were in the non-proliferative G0/G1 phase in the desferri-Exochelin group. In summary, after one day of treatment there were small shifts of cells out of the non-proliferative G0/G1 stage into the growth fraction in the control and deferoxamine groups, no change in the percentage of cells in the growth fraction in the ferri-Exochelin group, and a marked decrease in the percentage of cells in the growth fraction in the desferri-Exochelin group. Therefore, deferoxamine, while showing a lesser cell count than ferri-Exochelin, did not prevent shifts of cells into the growth fraction of the cell cycle, while the ferri-Exochelin slightly decreased the shift of cells into the growth fraction, and the desferri-Exochelin caused a dramatic alteration in the distribution, resulting in only a very small number of cells in the proliferative S/G2-M phases of the cell cycle after one day of treatment. This result is consistent with death of cells in the growth fraction of the cell cycle.

As has been demonstrated above, in cultured human breast cancer cells, the desferri-Exochelin resulted in considerable cell death over several days and a dramatic change in the distribution of the cells within the cell cycle on Day 1 compared with pretreatment values, with only a small percentage in the growth fraction and the vast majority in a non-proliferative phase. Deferoxamine decreased the rate of cell growth but did not cause cell death over the four day treatment period, and increased the percentage of cells in the growth fraction on Day 1. The ferri-Exochelin also decreased the rate of cell growth without causing cell death during the four day treatment period, but showed a decrease in the percentage of cells in the growth fraction.

Thus a desferri-Exochelin was highly effective both in killing and in inhibiting proliferation of a line of cancer cells. Although this probably was related, at least in part, to its capacity to chelate iron, the desferri-Exochelin was considerably more effective in preventing cell proliferation than another iron chelator, deferoxamine. While this could be a result of more efficient iron chelation by the lipid-soluble desferri-Exochelin, since the iron-loaded Exochelin also had some inhibitory effect on the proliferation of the cancer cells, it is concluded that the Exochelin molecule has an additional anti-cancer effect that is independent of its ability to chelate iron.

To demonstrate the superior effect of desferri-Exochelins on cells, the following comparative study was run against deferoxamine, a prior reported free radical scavenger.

The heart of a male rat was excised after the rat was anesthetized, a thoracotomy performed and the heart chilled in situ. The excised heart was then placed on a Langendorff apparatus and perfused with a collagenase and hyaluronidase in a 50 $\mu$M calcium in modified Krebs Ringer buffer solution. The tissue was then finely divided and dispersed in a collagenase/trypsin solution, filtered into a cold trypsin inhibitor solution and exposed to increasing concentrations of calcium. After removal of damaged cells, the remaining cell suspension was placed in several laminin-coated plastic dishes along with a culture medium containing 5% fetal bovine serum.

Figure 5:
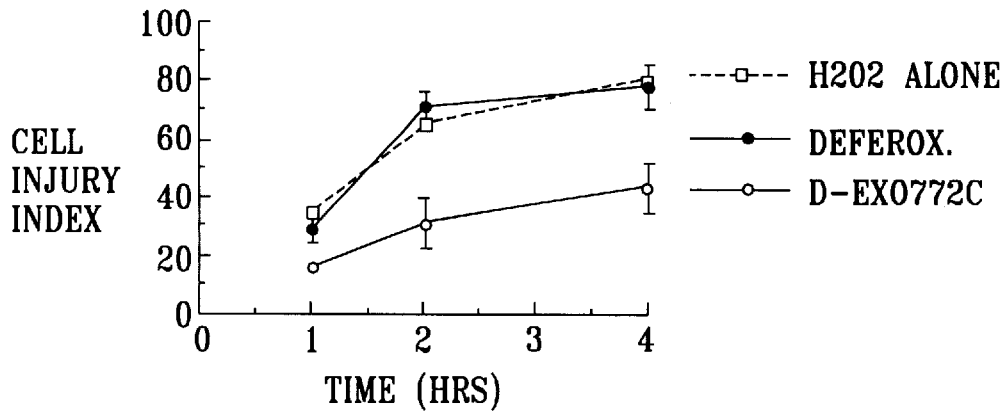
FIG. 5 is a graph showing the inhibition of oxidative cell injury to cardiac myocytes as the result of the use of an Exochelin mixture.

After the cultures were allowed to sit for 48 hours hydrogen peroxide was added to each dish and the lactate dehydrogenase activity (LDH), which is indicative of cell injury, was measured at various time intervals. A cell injury index (CII) for comparison purposes was obtained by measuring the LDH in a nonexposed cell culture in both an as is condition (0 Index) and following exposure to a detergent that lyses 100% of the myocytes (1% Triton X-100) representing a CII of 100. The LDH under specified treatment conditions for various periods of time was then determined, the corresponding CII value determined and the individual results were plotted against time (FIG. 5).

Desferri-form of Exochelins 772C, a relatively non-polar substance, was isolated and used to treat cell cultures. The Exochelin were converted to the desferri-Exochelin form by incubation for several days with 50 millimolar EDTA at pH 6. The desferri-form was then repurified by chloroform extraction.

Three samples of cells were exposed to either a) $H_2O_2$, b) deferoxamine added 20 minutes after $H_2O_2$ addition or c) a smaller amount of desferri-Exochelin added 20 minutes after $H_2O_2$ addition to the cell culture. The untreated cell culture showed about 80% cell injury over a 4 hour period. Plotted in FIG. 5 are the results for 20 minute delayed delivery of the Exochelins. Exochelin 772C shows retardation of injury while deferoxamine added at the same time showed no beneficial effect. It is therefore concluded that the relatively non-polar, more lipid soluble Exochelins are effective when administered with or after formation of the (●OH) radical, i.e., after injury occurs. The Exochelins' lipid solubility provides the ability to rapidly enter cells and reduce or prevent cell damage while deferoxamine administered under the same conditions is ineffective to protect the cells.

Because of the aqueous and lipid solubility of the Exochelins and ferri-Exochelins, they may be delivered by all recognized drug delivery means including direct injection into the tumor site, in intravenous solutions or orally.

Although the present invention has been described in considerable detail with reference to certain preferred versions and uses thereof, other versions and uses are possible. Therefore, the spirit and scope of the appended claims should not be limited to the description of the preferred versions contained herein.

What is claimed is:

1. A method of treating cancer in a patient in need of such treatment, comprising administering to said patient a composition comprising a solution containing an amount of a desferri-Exochelin effective to inhibit the growth of and/or kill cancer cells.

2. The method of claim 1 wherein the composition is delivered by intravenous, direct placement or oral means of administration.

3. The method of claim 1 wherein the desferri-Exochelin is generated from and purified from a strain of *M. tuberculosis*.

4. The method of claim 1 wherein the desferri-Exochelin has a mass of 717 Daltons.

5. The method of claim 1 wherein the desferri-Exochelin contains bound iron.

* * * * *